(12) United States Patent
Hamann et al.

(10) Patent No.: US 11,666,667 B2
(45) Date of Patent: Jun. 6, 2023

(54) PATCHES COMPRISING URUSHIOL, TEST PANELS COMPRISING THE SAME, AND METHODS OF USING THE SAME

(71) Applicant: HAPTEN SCIENCES, INC., Memphis, TN (US)

(72) Inventors: Curt Hamann, Phoenix, AZ (US); Mahmoud Ahmed Elsohly, Oxford, MS (US); Waseem Gul, Oxford, MS (US); Raymond J. Hage, Bryn Mawr, PA (US)

(73) Assignee: HAPTEN SCIENCES, INC., Memphis, TN (US)

( * ) Notice: Subject to any disclaimer, the term of this patent is extended or adjusted under 35 U.S.C. 154(b) by 69 days.

(21) Appl. No.: 16/969,850

(22) PCT Filed: Feb. 13, 2019

(86) PCT No.: PCT/US2019/017835
§ 371 (c)(1),
(2) Date: Aug. 13, 2020

(87) PCT Pub. No.: WO2019/160942
PCT Pub. Date: Aug. 22, 2019

(65) Prior Publication Data
US 2020/0405886 A1 Dec. 31, 2020

Related U.S. Application Data (60) Provisional application No. 62/630,151, filed on Feb. 13, 2018.

(51) Int. Cl.
*A61K 49/00* (2006.01)
*A61K 9/00* (2006.01)
*A61K 9/70* (2006.01)
*A61K 31/05* (2006.01)

(52) U.S. Cl.
CPC ........ *A61K 49/0006* (2013.01); *A61K 9/0014* (2013.01); *A61K 9/7069* (2013.01); *A61K 31/05* (2013.01)

(58) Field of Classification Search
CPC .............. A61K 49/0006; A61K 9/0014; A61K 9/7069; A61K 31/05
See application file for complete search history.

(56) References Cited

U.S. PATENT DOCUMENTS

| | | |
|---|---|---|
| 5,409,908 A | 4/1995 | Sanchez et al. |
| 8,486,998 B2 | 7/2013 | Elsohly et al. |
| 9,029,417 B2 | 5/2015 | Elsohly et al. |
| 9,408,822 B2 | 8/2016 | Elsohly et al. |
| 2004/0047902 A1 | 3/2004 | Dupont et al. |

FOREIGN PATENT DOCUMENTS

| | | |
|---|---|---|
| CN | 103479400 A | 1/2014 |
| WO | WO 00/37067 A1 | 6/2000 |

OTHER PUBLICATIONS

Dahl et al., "Toxicodendron Antigen Patch Test," Arch Dermatol. 1984; 120: 1022-1024.
Elsohly et al., "Separation and Characterization of Poison Ivy and Poison Oak Components," Journal of Natural Products, 1982; 45(5): 532-538.
Epstein et al., "Poison Oak Hyposensitization," Arch. Dermatol., Mar. 1974, 109:356-360.
International Search Report and Written Opinion of the International Searching Authority for International Application No. PCT/US2019/17835 dated May 7, 2019.
Sawhney et al., "Bioerodible Hydrogels Based on Photopolymerized Poly(ethylene glycol)-co-poly($\alpha$-hydroxy acid) Diacrylate Macromers," Macromolecules, 1993, 26:581-587.
Smith et al., "Lack of Efficacy of a Barrier Cream in Preventing Rhus Dermatitis," Arch Dermatol., Jun. 1993, 129: 787-788.
Williams et al., "Individual Variations in Allergic Contact Dermatitis from Urushiol," Arch Dermatol. Aug. 1999, 135(8): 1002-1003.
T.R.U.E. Test, Package Insert, Highlights of Prescribing Information, Aug. 2017, 28 pages.
Kim and Shin, "Results of patch test with urushiol in Korean," Contact Dermatitis, 2014, 70 (Suppl. 1), p. 74, Abstract No. 114.
Smartpractice, T.R.U.E. Test Thin-Layer Rapid Use Epicutaneous Patch Test, Reference Manual, 2015, 115 pages.

*Primary Examiner* — Robert S Cabral
(74) *Attorney, Agent, or Firm* — Cooley LLP (57) ABSTRACT

Disclosed herein are urushiol-containing epicutaneous patches comprising a support material and a urushiol-containing film on a surface of the support material. A surface of the support material is coated with the urushiol-containing film. Also described herein are test panels comprising urushiol-containing epicutaneous patches of varying urushiol content. The test panels can be employed in methods to assess subject sensitivity to urushiol, to determine a dose-response relationship to varying doses of urushiol, and to assess efficacy of treatments to prevent or inhibit urushiol-induced contact dermatitis in a subject.

19 Claims, 7 Drawing Sheets

PATCHES COMPRISING URUSHIOL, TEST PANELS COMPRISING THE SAME, AND METHODS OF USING THE SAME

CROSS-REFERENCE TO RELATED APPLICATIONS

This application is a National Stage Application under 35 U.S.C. § 371 of International Application No. PCT/US2019/017835, filed Feb. 13, 2019, which claims the benefit of U.S. Provisional Application No. 62/630,151, filed on Feb. 13, 2018, the disclosures of which are hereby incorporated by reference herein in their entireties for all purposes.

BACKGROUND OF THE DISCLOSURE

Poison ivy, poison oak, and poison sumac are the most common causes of allergic contact dermatitis in North America, affecting 10-50 million Americans per year.[1] Prevalence of poison ivy and poison oak sensitivity in the general adult population ranges from 50-70%.[2,3] Poison ivy dermatitis affects all ethnicities and skin types and most geographical regions in the United States are at risk.[4] Plant dermatitis is a significant occupational hazard in agriculture and forestry and afflicts many individuals engaged in outdoor or wilderness activities. Furthermore, this can result in significant monetary expense for worker disability and medical therapy.[5]

Figure 1:
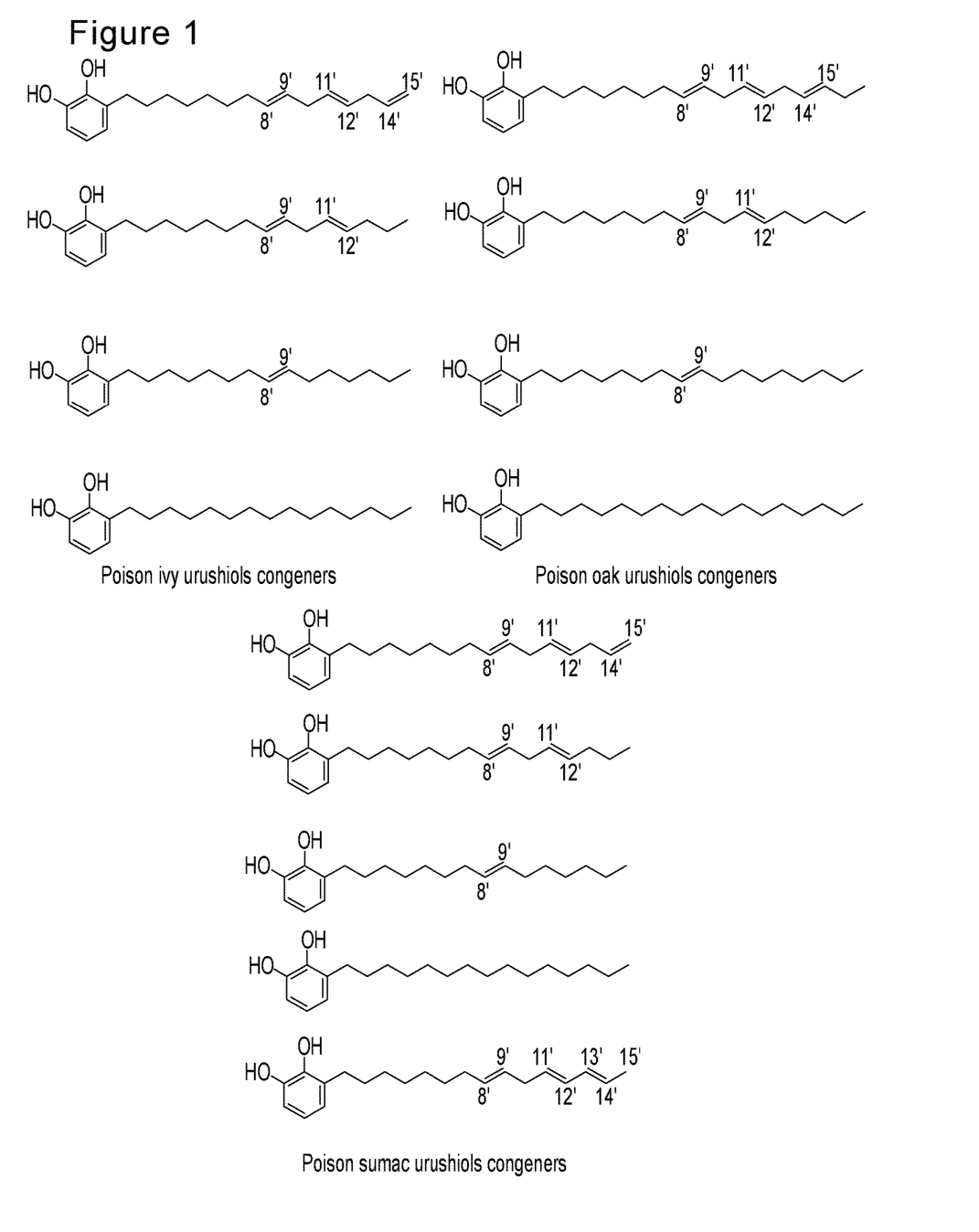
FIG. 1 shows structures of urushiol compounds.

Poison ivy, poison oak and poison sumac are members of the Anacardiaceae family of plants and belong to the genus *Toxicodendron*.[3] Exposure to plants of the Anacardiaceae family account for more allergic contact dermatitis than all other plant families combined.[5] The allergens, called urushiol, responsible for causing allergic contact dermatitis to poison ivy, oak, and sumac are found in the plants' sap material. Urushiol is an oily mixture of organic compounds (referred to herein collectively as "urushiol," "urushiols" and/or "urushiol oil") that exhibit allergenic properties. Urushiol is composed of a mixture of catechols with either a 15- or 17-carbon side chain at the C-3 position, with one, two, three or more olefins. Poison ivy urushiol contains predominantly 3-n-pentadecylcatechols (C-15) and poison oak contains mainly 3-n-heptadecylcatechols (C-17)[2,3] (see, e.g., FIG. 1). Because urushiol in poison ivy, poison oak, and poison sumac differ only slightly in structure, they can cross-react, and thus, an individual who is sensitized to one may react to all.

Allergic contact dermatitis from poison ivy, oak or sumac is a classic type IV hypersensitivity (cell-mediated) allergic reaction. Because urushiol is a powerful antigen, a single exposure can be adequate to cause clinical symptoms. Re-exposure to poison ivy causes cytokine release and clinical symptoms in 12 to 48 hours. Clinical presentation is classically an acute eczematous eruption characterized by linear streaks of erythematous papules and vesicles where the plant has brushed the skin. Secondary changes include weeping, crusting, edema, and excoriations. The eruption generally begins 24 to 48 hours after contact with the plant and if left untreated, the eruption can last up to 3 weeks.[3]

Although urushiol is degraded by water, it must be washed off immediately.[14] 50% can be removed at 10 minutes, 25% at 15 minutes and 10% at 30 minutes.[10] After 30 minutes, all of the oil is absorbed. Post-exposure therapies include those that prevent a response and those that provide symptomatic relief. Therapies aimed at preventing a response have been found to provide protection from developing a reaction. However, studies that assessed such therapies not only had small sample sizes but also did not result in protection for all subjects who used these products.[15,16] Symptomatic relief of pruritus includes tepid baths with baking soda or colloidal oatmeal, cool compresses, calamine lotion, topical or systemic antihistamines, astringent solutions, topical calcineurin inhibitors and topical or systemic steroids.[10] Systemic corticosteroids are the mainstay of treatment in moderate to severe contact dermatitis, and are typically given for 7-10 days, followed by a taper of another 7-10 days.

Preventive methods include fabrics, barrier creams, and desensitization programs. Dry, loosely woven fabrics are most protective as opposed to sweaty, thin clothing, where the antigen can easily soak through the cloth and deposit on the skin before being broken down.[10] The ideal barrier cream is described to be an effective, non-sensitizing, non-irritating, easily applied and removed, cosmetically acceptable and cost-efficient.[17] The only FDA approved barrier product, quaternium-18-bentonite, was shown to be highly effective in preventing experimentally produced allergic contact dermatitis to urushiol.[18] Unfortunately, the limitation with barrier products, such as quaternium-18-bentonite, is that subjects must preemptively use these products before being exposed to the allergen. Furthermore, desensitization programs for sensitized individuals have not demonstrated to be promising methods of prevention to date.[14,19]

Although many methods and treatments have been developed to destroy the plant or protect the subject, none have been proven to be wholly effective.[20] The only infallible method is complete avoidance. Extensive efforts have been made to develop therapies to prevent and/or mitigate urushiol-induced contact dermatitis resulting from exposure to poison ivy, oak and sumac. At the present time there is no urushiol sensitivity patch test available in the United States to assess the efficacy of such therapies.

To accurately evaluate the efficacy of new therapies for preventing or mitigating urushiol-induced contact dermatitis, appropriate assessment tools and methods are needed to quantify baseline response to urushiol exposure and to evaluate the effect of experimental treatments for urushiol exposure. Moreover, such tools and methods are needed to identify urushiol-induced contact dermatitis and distinguish urushiol-induced contact dermatitis from other types of dermatitis to effectively treat subjects presenting dermatitis of unknown etiology.

SUMMARY OF THE DISCLOSURE

In a first aspect, the present disclosure provides a urushiol-containing epicutaneous patch comprising a support material and a urushiol-containing film on a surface of the support, wherein a surface of the support material is coated with the urushiol-containing film. In some embodiments, the urushiol-containing film is affixed to a surface of the support material. In some embodiments, the urushiol-containing film comprises a carrier material. In some embodiments, the carrier material comprises polyvinylpyrrolidone.

In some embodiments, the urushiol comprises one or more of pentadecylcatechol, mono-, di-, or tri-unsaturated congeners of pentadecylcatechol. In some embodiments, the urushiol-containing film comprises from about 0.02 µg to about 100 µg of urushiol. In some embodiments, the urushiol-containing film comprises from about 0.04 µg to about 0.5 µg of urushiol. In some embodiments, urushiol-containing film comprises about 0.041 µg of urushiol. In some embodiments, the urushiol-containing film comprises from about 0.075 µg to about 0.085 µg of urushiol. In some embodiments, the urushiol-containing film comprises about 0.081 µg of urushiol. In some embodiments, the urushiol-containing film comprises from about 0.1 µg to about 0.2 µg of urushiol. In some embodiments, the urushiol-containing film comprises about 0.16 µg of urushiol. In some embodiments, the urushiol-containing film comprises from about 0.3 µg to about 0.4 µg of urushiol. In some embodiments, the urushiol-containing film comprises about 0.32 µg of urushiol. In some embodiments, the urushiol is uniformly distributed throughout the carrier material of the urushiol-containing film.

In some embodiments, the support material comprises a polyester. In some embodiments, the support material comprises an occlusive polyester. In some embodiments, the support material is occlusive Melinex® polyester. In some embodiments, the patch has a size of from about 0.2 $cm^2$ to about 1 $cm^2$. In some embodiments, the patch has a size of from about 0.5 $cm^2$ to about 0.9 $cm^2$. In some embodiments, the patch has a size of about 0.81 $cm^2$.

In another aspect, the present disclosure provides a test panel for assessment of allergic contact dermatitis in a subject resulting from exposure to urushiol, comprising at least 1 urushiol-containing epicutaneous patch. In some embodiments, the test panel comprises at least 2 urushiol-containing epicutaneous patches, wherein each patch comprises a different amount of urushiol. In some embodiments, the test panel comprises at least 3 urushiol-containing epicutaneous patches, wherein each patch comprises a different amount of urushiol. In some embodiments, the test panel comprises at least 4 urushiol-containing epicutaneous patches; wherein each patch comprises a different amount of urushiol. In some embodiments, the test panel further comprises a control patch substantially identical to the urushiol-containing epicutaneous patches, but which does not contain urushiol.

In some embodiments, the urushiol-containing epicutaneous patches are affixed to a surface of an adhesive support. In some embodiments, the adhesive support comprises an adhesive tape. In some embodiments, the adhesive tape is surgical tape.

In some embodiments, the test panel comprises a first patch comprising about 0.041 µg of urushiol, a second patch comprising about 0.081 µg of urushiol, a third patch comprising about 0.16 µg of urushiol, a fourth patch comprising about 0.32 µg of urushiol; and a control patch substantially identical to said first, second, third, and fourth patches, but which does not contain urushiol.

In another aspect, the present disclosure provides a method for assessing sensitivity to urushiol-induced allergic contact dermatitis in a subject, comprising applying a test panel as described herein to the skin of the subject for a predetermined period of time, removing the test panel from the skin of the subject, and evaluating the severity of allergic contact dermatitis of the subject at the point of contact of each patch of the test panel at one or more times after removal of the test panel. In some embodiments, the predetermined period of time is from about 1 hour to about 96 hours. In some embodiments, the predetermined period of time is from about 24 hours to about 72 hours. In some embodiments, the predetermined period of time is about 48 hours. In some embodiments, the evaluating is conducted immediately after removal of the test panel from the subject's skin. In some embodiments, the evaluating is conducted on one or more of days 2-30 after removal of the test panel from the subject's skin. In some embodiments, the evaluating is conducted on each of days 2, 4, 7, 14, and 21 after removal of the test panel from the subject's skin.

In another aspect, the present disclosure provides a method for calculating a dose-response for urushiol exposure and resulting severity of allergic contact dermatitis in a subject, comprising applying a test panel as described herein for a predetermined period of time, removing the test panel from the skin of the subject, quantifying the severity of allergic contact dermatitis of the subject at the point of contact of each patch of said test panel, correlating the quantitative severity of allergic contact dermatitis at the location of contact of each patch of said test panel to the urushiol content of each patch corresponding to said location of contact of each patch, and calculating a dose-response for urushiol exposure and resulting allergic contact dermatitis in a subject from said quantified severity of allergic contact dermatitis to the urushiol content of each patch at the location corresponding to said quantified severity.

In some embodiments, the predetermined period of time is from about 1 hour to about 96 hours. In some embodiments, the predetermined period of time is from about 24 hours to about 72 hours. In some embodiments, the predetermined period of time is about 48 hours.

In another aspect, the present disclosure provides a method for determining if dermatitis of unknown etiology on the skin of a subject presenting with said dermatitis of unknown etiology at one or more locations on the skin of the subject is urushiol-induced allergic contact dermatitis, comprising a test panel as described herein to the skin of the subject for a predetermined period of time, evaluating the urushiol-induced allergic contact dermatitis of the subject at the point of contact of each patch of the test panel, and comparing the urushiol-induced allergic contact dermatitis at the point of contact of each patch of the test panel with the dermatitis of unknown etiology at one more locations on the skin of the subject, wherein when the dermatitis at the point of contact of each patch of the test panel is substantially similar to the dermatitis at one more locations on the skin of the subject, the dermatitis of unknown etiology is urushiol-induced allergic contact dermatitis.

In some embodiments, the predetermined period of time is from about 1 hour to about 96 hours. In some embodiments, the predetermined period of time is from about 24 hours to about 72 hours. In some embodiments, the predetermined period of time is about 24 hours. In some embodiments, the predetermined period of time is about 48 hours.

In another aspect, the present disclosure provides a method for determining if a treatment for urushiol-induced allergic contact dermatitis prevents or inhibits the severity of the urushiol-induced allergic contact dermatitis in a subject, comprising applying a test panel as described herein to the skin of the subject for a predetermined period of time, removing the test panel from the skin of the subject, evaluating the severity of allergic contact dermatitis of the subject at the point of contact of each patch of the test panel at one or more times after removal of the test panel, administering the treatment to the subject, applying a test panel as described herein to the skin of the subject for the same predetermined period of time after administering the treatment, removing the test panel from the skin of the subject, and evaluating the severity of allergic contact dermatitis of the subject at the point of contact of each patch of the test panel at one or more times after administering the treatment, wherein when the severity of allergic contact dermatitis of the subject at the point of contact of each patch of the test panel applied after said administering step is less than the severity of allergic contact dermatitis of the subject at the point of contact of each patch of the test panel applied before said administering step, the treatment is determined to prevent or inhibit the severity of urushiol-induced allergic contact dermatitis in the subject.

In some embodiments, the predetermined period of time is from about 1 hour to about 96 hours. In some embodiments, the predetermined period of time is from about 24 hours to about 72 hours. In some embodiments, the predetermined period of time is about 48 hours. In some embodiments, the evaluating is conducted immediately after removal of the test panel from the subject's skin. In some embodiments, the evaluating is conducted on one or more of days 2-30 after removal of the test panel from the subject's skin. In some embodiments, the evaluating is conducted on each of days 2, 4, 7, 14, and 21 after removal of the test panel from the subject's skin.

In some embodiments, the urushiol in the patches, test panels, or methods described herein comprises one or more of pentadecylcatechol, mono-, di-, or tri-unsaturated congeners of pentadecylcatechol, or combinations thereof.

DETAILED DESCRIPTION

It will be understood by one of ordinary skill in the relevant arts that other suitable modifications and adaptations to the compositions and methods described herein are readily apparent from the description of the invention contained herein in view of information known to the ordinarily skilled artisan and may be made without departing from the scope of the invention or any embodiment thereof.

Definitions

The term "about" means ±10% of a value. Thus, for example, about 100 means from 90 to 110, and from about 100 to about 200 includes from 90 to 220.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

The term "urushiol" as used herein means a mixture of catechols with either a 15- or 17-carbon side chain at the C-3 position, which may contain one or more degrees of unsaturation. Poison ivy urushiol contains predominantly 3-n-pentadecylcatechols (C-15) and poison oak contains mainly 3-n-heptadecylcatechols (C-17)[2,3] (see, e.g., FIG. 1). Because urushiol in poison ivy, poison oak, and poison sumac differ only slightly in structure, they can cross-react, and thus, an individual who is sensitized to one may react to all.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b)

inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In certain embodiments a subject is a human.

In certain embodiments, the subject is a human.

As used herein, "administering" has its usual meaning and encompasses administering by any suitable route of administration, including, without limitation, intravenous, intramuscular, intraperitoneal, intrathecal, intraocular (e.g., intravitreal), subcutaneous, direct injection (for example, into a tumor), mucosal, inhalation, oral, and topical.

Non-biodegradable and biodegradable polymeric materials can be used in the manufacture of patches as described herein. Such polymers may be natural or synthetic polymers. Bioadhesive polymers include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly (methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Urushiol-Containing Epicutaneous Patches

In a first aspect, the present disclosure provides a urushiol-containing epicutaneous patch (or "patch") comprising a support material and a urushiol-containing film on a surface of the support, wherein a surface of the support material is coated with the urushiol-containing film.

In some embodiments, the urushiol-containing film comprises a carrier material. In some embodiments, the carrier material comprises a hydrogel. In some embodiments, the hydrogel is selected from the group consisting of polyvinyl alcohol, sodium polyacrylate, acrylate copolymers, polyvinylpyrolidone, maleic anhydride polyvinylpyrrolidone, or mixtures thereof. In some embodiments, the carrier material is polyvinylpyrrolidone.

In some embodiments, the urushiol-containing film comprises from about 0.001 μg to about 100 μg of urushiol. In some embodiments, the urushiol-containing film comprises about 0.001, about 0.005, about 0.010, about 0.015, about 0.020, about 0.025, about 0.030, about 0.035, about 0.040, about 0.045, about 0.050, about 0.060, about 0.070, about 0.080, about 0.090, about 0.1, about 0.15, about 0.2, about 0.25, about 0.3, about 0.35, about 0.4, about 0.45, about 0.5, about 0.6, about 0.7, about 0.8, about 0.9, about 1, about 3, about 4, about 5, about 10, about 20, about 30, about 40, about 50, about 60, about 70, about 80, about 90, or about 100 μg of urushiol.

In some embodiments, the urushiol-containing film comprises from about 0.04 μg to about 0.5 μg of urushiol. In some embodiments, urushiol-containing film comprises about 0.041 μg of urushiol. In some embodiments, the urushiol-containing film comprises from about 0.075 μg to about 0.085 μg of urushiol. In some embodiments, the urushiol-containing film comprises about 0.081 μg of urushiol. In some embodiments, the urushiol-containing film comprises from about 0.1 μg to about 0.2 μg of urushiol. In some embodiments, the urushiol-containing film comprises about 0.16 μg of urushiol. In some embodiments, the urushiol-containing film comprises from about 0.3 μg to about 0.4 μg of urushiol. In some embodiments, the urushiol-containing film comprises about 0.32 μg of urushiol. In some embodiments, the urushiol is uniformly distributed throughout the carrier material of the urushiol-containing film.

In some embodiments, the urushiol-containing film is applied to a surface of the support material. Any suitable application method including screen printing, offset printing, roll printing, or other well-known techniques for applying liquids or gels to a substrate may be employed. In some embodiments, the urushiol-containing film is affixed to a surface of the support material. The film may be affixed by contacting the film material with the support material.

The support material may comprise any impermeable material having suitable properties to allow application of the urushiol-containing film and subsequent cutting to provide a patch having a desired size.

Any suitable material can be used as a support material. In some embodiments, the support material exhibits electrostatic properties to improve adhesion of the urushiol-containing film to the support material. In other embodiments, the support material does not exhibit electrostatic properties. In some embodiments, the support material may comprise a polymer including cellulose plastics (CA, CP), polyethylene (PE), polyethylene terephtalate (PET), polyvinyl chlorides (PVCs), polypropylenes, polystyrenes, polycarbonates, polyacrylics, and poly(methylmethacrylate) (PMMA), fluoropolymers (PTFE for example), or polyvinylpyrolidones.

The support material may be rigid or flexible, may or may not be hydrophilic, and may or may not be translucent, depending on the material. In one embodiment, a transparent support material is chosen, thus making it possible in certain circumstances (e.g., in combination with a translucent adhesive support for the patch in a test panel as described herein) to directly observe the appearance of skin reaction to the patch, without necessarily having to remove the patch of the test panel.

In some embodiments, the support material comprises a polyester. In some embodiments, the support material comprises an occlusive polyester. In some embodiments, the support material is occlusive Melinex® polyester.

The patch may have any dimensions which are amenable to placement on the adhesive support of a test panel described herein. Thus, in some embodiments, the patch has a size of from about 0.1 $cm^2$ to about 1 $cm^2$. In some embodiments, the patch has a size of from about 0.1 $cm^2$ to about 0.9 $cm^2$. In some embodiments, the patch has a size of from about 0.1 $cm^2$ to about 0.8 $cm^2$. In some embodiments, the patch has a size of from about 0.1 $cm^2$ to about 0.7 $cm^2$. In some embodiments, the patch has a size of from about 0.1 $cm^2$ to about 0.6 $cm^2$. In some embodiments, the patch has a size of from about 0.1 $cm^2$ to about 0.5 $cm^2$. In some embodiments, the patch has a size of from about 0.1 $cm^2$ to about 0.4 $cm^2$. In some embodiments, the patch has a size of from about 0.1 $cm^2$ to about 0.3 $cm^2$. In some embodiments, the patch has a size of from about 0.1 $cm^2$ to about 0.2 $cm^2$.

In some embodiments, the patch has a size of from about 0.5 $cm^2$ to about 0.9 $cm^2$. In some embodiments, the patch has a size of about 0.81 $cm^2$. The patch may have a square shape, a rectangular shape, a circular shape, an oval shape, or any other suitable shape. In some embodiments, the patch has a square shape. Moreover, for test panels having multiple patches affixed thereto, in some embodiments each patch may have the same size. In some embodiments each patch may have the same shape. In other embodiments, each patch may individually have a particular size. Similarly, in other embodiments, each patch may individually have a particular shape.

In some embodiments, patches may have a particular shape and/or size corresponding to the concentration of urushiol contained therein. Thus, in some embodiments, a patch having a first amount of urushiol may have a first shape and/or size, and a patch having a second amount of urushiol may have a second shape and/or size, wherein the first and second amount of urushiol are different. The use of different shapes and sizes correlating to different amount of urushiol contained in different shape or size patches may enable ease of identification of patch concentration. For example, a first patch comprising about 0.1 µg of urushiol may be square and have a size of about 0.5 $cm^2$, and a second patch comprising about 0.3 µg of urushiol may be circular and have a size of about 0.5 $cm^2$. Alternatively, a patch comprising about 0.1 µg of urushiol may be square and have a size of about 0.5 $cm^2$, and a second patch comprising about 0.3 µg of urushiol may also be square and have a size of about 1.0 $cm^2$. As can be easily understood by those skilled in the art, combinations of size and shape corresponding to particular amounts of urushiol can allow for ready identification of patch concentration either alone, or on a test panel with 1 or more other patches.

Test Panels

In another aspect, the present disclosure provides a test panel for assessment of allergic contact dermatitis in a subject resulting from exposure to urushiol, comprising at least 1 urushiol-containing epicutaneous patch ("patch") as described herein.

In some embodiments, the test panel comprises 1, 2, 3, 4, 5 6, 7, 8, 9, or 10 urushiol-containing epicutaneous patches. In some embodiments, each patch on the test panel may have any dimensions which are amenable to placement on the adhesive support of a test panel described herein. Thus, in some embodiments, each patch on the test panel independently has a size of from about 0.1 $cm^2$ to about 1 $cm^2$. In some embodiments, each patch on the test panel independently has a size of from about 0.1 $cm^2$ to about 0.9 $cm^2$. In some embodiments, each patch on the test panel independently has a size of from about 0.1 $cm^2$ to about 0.8 $cm^2$. In some embodiments, each patch on the test panel independently has a size of from about 0.1 $cm^2$ to about 0.7 $cm^2$. In some embodiments, each patch on the test panel independently has a size of from about 0.1 $cm^2$ to about 0.6 $cm^2$. In some embodiments, each patch on the test panel independently has a size of from about 0.1 $cm^2$ to about 0.5 $cm^2$. In some embodiments, each patch on the test panel independently has a size of from about 0.1 $cm^2$ to about 0.4 $cm^2$. In some embodiments, each patch on the test panel independently has a size of from about 0.1 $cm^2$ to about 0.3 $cm^2$. In some embodiments, each patch on the test panel independently has a size of from about 0.1 $cm^2$ to about 0.2 $cm^2$.

In some embodiments, each patch on the test panel independently has a size of from about 0.5 $cm^2$ to about 0.9 $cm^2$. In some embodiments, each patch on the test panel has a size of about 0.81 $cm^2$. In some embodiments, each patch on the test panel has a square shape. For test panels having multiple patches affixed thereto, each patch on the test panel may have the same size. In some embodiments, each patch on the test panel has the same shape. In other embodiments, each patch on the test panel may individually have a particular size. Similarly, in other embodiments, each patch on the test panel may independently have a particular shape.

In some embodiments, each patch on the test panel may have a particular shape and/or size corresponding to the concentration of urushiol contained in each shape of patch. Thus, in some embodiments, a test panel may comprise a first patch may have a first amount of urushiol and a first shape and/or size, and second patch having a second amount of urushiol and a second shape and/or size, wherein the first and second amount of urushiol are different. The use of different shapes and sizes correlating to different amount of urushiol contained in different shape or size patches may enable ease of identification of patch concentration. For example, a first patch on a test panel comprising about 0.1 µg of urushiol may be square and have a size of about 0.5 $cm^2$, and a second patch on the same test panel comprising about 0.3 µg of urushiol may be circular and have a size of about 0.5 $cm^2$. Alternatively, a first patch on a test panel comprising about 0.1 µg of urushiol may be square and have a size of about 0.5 $cm^2$, and a second patch on a test panel comprising about 0.3 µg of urushiol may also be square and have a size of about 1.0 $cm^2$. As can be easily understood by those skilled in the art, us of combinations of size and shape corresponding to particular amounts of urushiol for patches can allow for ready identification of patch concentration on a test panel containing two or more patches.

In some embodiments, the test panel comprises at least 2 urushiol-containing epicutaneous patches, wherein each patch comprises a different amount of urushiol. In some embodiments, the test panel comprises at least 3 urushiol-containing epicutaneous patches, wherein each patch comprises a different amount of urushiol. In some embodiments, the test panel comprises at least 4 urushiol-containing epicutaneous patches; wherein each patch comprises a different amount of urushiol. In some embodiments, the test panel further comprises a control patch substantially identical to the urushiol-containing epicutaneous patches, but which does not contain urushiol. In some embodiments, the test panel comprises 4 urushiol-containing epicutaneous patches; wherein each patch comprises a different amount of urushiol, and a control patch.

In some embodiments, the urushiol-containing epicutaneous patches are affixed to a surface of an adhesive support. The adhesive support may be any suitable support having an adhesive affixed to a surface of the support. In some embodiments, the adhesive support comprises an adhesive tape. In some embodiments, the adhesive tape is surgical tape. As will be appreciated by those skilled in the art, a suitable tape must be one to which one or more patches can be affixed, wherein the surfaces not covered by patches can adhere to a subject's skin. Accordingly, the size of the adhesive support can be of any dimension sufficient to adhere a desired number of patches to a surface of the test panel, with sufficient surface to adhere the test panel to the skin of the subject. In one embodiment, the adhesive support of the test panel exhibits sufficient adhesion to the subject's skin to allow for epicutaneous delivery of the urushiol contained in the patch(es) affixed to the test panel.

Patches may be affixed in any pattern on the surface of adhesive support of the test patch. For example, the patches may be substantially aligned longitudinally along the adhesive support of the test panel. Alternatively, in some embodiments the patches may be affixed and oriented randomly to the surface of the adhesive support.

The distance between the any two adjacent patches should be sufficient to maintain contact of each patch with the subject's skin. In addition, the distance between adjacent patches should be sufficient to allow for clear, independent assessment of the dermatitis on subject's skin at each patch site. Thus, in some embodiments, the distance between adjacent patches may be from about 0.1 cm to about 5 cm. In some embodiments, the the distance between adjacent patches may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5 cm. In embodiments where three or more patches are present, the distance between, e.g., first and second adjacent patches may be the same as the distance between the second and third adjacent patches on the test panel. In embodiments where three or more patches are present, the distance between, e.g., first and second adjacent patches may be different than the distance between the second and third adjacent patches on the test panel.

Moreover, the distance between the edge of any patch and the edge of the adhesive support should be sufficient to allow adhesion to the subject's skin of the test panel. Thus, in some embodiments, the distance between the edge of any patch and the edge of the adhesive support may be from about 0.1 cm to about 5 cm. In some embodiments, the distance between the edge of any patch and the edge of the adhesive support may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5 cm.

In some embodiments, the test panel comprises a first patch comprising about 0.041 µg of urushiol, a second patch comprising about 0.081 µg of urushiol, a third patch comprising about 0.16 µg of urushiol, a fourth patch comprising about 0.32 µg of urushiol; and a control patch substantially identical to said first, second, third, and fourth patches, but which does not contain urushiol. In some embodiments, each of the four patches and the control patch has a square shape and a size of about 0.81 cm$^2$.

Methods of Use

In another aspect, the present disclosure provides a method for assessing sensitivity to urushiol-induced allergic contact dermatitis in a subject, comprising applying a test panel as described herein to the skin of the subject for a predetermined period of time, removing the test panel from the skin of the subject, and evaluating the severity of allergic contact dermatitis of the subject at the point of contact of each patch of the test panel at one or more times after removal of the test panel.

In some embodiments, the test panel is placed in contact with a subject's skin for predetermined period of time from about 1 hour to about 96 hours. In some embodiments, the predetermined period of time is from about 24 hours to about 72 hours. In some embodiments, the predetermined period of time is about 24, about 48, about 72, or about 96 hours. After removing the test panel from the subject's skin, the severity of the urushiol-induced contact dermatitis induced by each patch on the test panel is assessed. Such assessment can comprise visual inspection of the area in contact with each patch on the test panel and assigning a score to the reaction associated with each patch based on inspection. Severity of the urushiol-induced contact dermatitis induced by each patch on the test panel of reactions is independently graded according to standard morphology: 0 (no reaction), 1+ (non-vesicular with erythema, infiltration, and possibly papules), 2+ (edematous or vesicular reaction), 3+ (spreading, bullous, ulcerative reaction), +/− (macular erythema).

In some embodiments, the evaluating is conducted immediately after removal of the test panel from the subject's skin. In some embodiments, the evaluating is conducted one or more times. In some embodiments, the evaluating is conducted immediately after removal of the test panel from the subject's skin and on one or more of more of days 2-30 after removal of the test panel from the subject's skin. In some embodiments, the evaluating is conducted on each of days 2, 4, 7, 14, and 21 after removal of the test panel from the subject's skin. In some embodiments, evaluating is conducted on one or more of day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, or day 30 after removal of the test panel from the subject's skin.

In another aspect, the present disclosure provides a method for calculating a dose-response for urushiol exposure and resulting severity of allergic contact dermatitis in a subject, comprising applying a test panel as described herein for a predetermined period of time, removing the test panel from the skin of the subject, quantifying the severity of allergic contact dermatitis of the subject at the point of contact of each patch of said test panel, correlating the quantitative severity of allergic contact dermatitis at the location of contact of each patch of said test panel to the urushiol content of each patch corresponding to said location of contact of each patch, and calculating a dose-response for urushiol exposure and resulting allergic contact dermatitis in a subject from said quantified severity of allergic contact dermatitis to the urushiol content of each patch at the location corresponding to said quantified severity.

In some embodiments, the test panel is placed in contact with a subject's skin for predetermined period of time from about 1 hour to about 96 hours. In some embodiments, the predetermined period of time is from about 24 hours to about 72 hours. In some embodiments, the predetermined period of time is about 24, about 48, about 72, or about 96 hours. After removing the test panel from the subject's skin, the severity of the urushiol-induced contact dermatitis induced by each patch on the test panel is assessed. Such assessment can comprise visual inspection of the area in contact with each patch on the test panel and assigning a score to the reaction associated with each patch based on inspection. Severity of the urushiol-induced contact dermatitis induced by each patch on the test panel of reactions is independently graded according to standard morphology: 0 (no reaction), 1+ (non-vesicular with erythema, infiltration, and possibly papules), 2+ (edematous or vesicular reaction), 3+ (spreading, bullous, ulcerative reaction), +/− (macular erythema).

In some embodiments, the evaluating is conducted immediately after removal of the test panel from the subject's skin. In some embodiments, the evaluating is conducted one or more times. In some embodiments, the evaluating is conducted immediately after removal of the test panel from the subject's skin and on one or more of more of days 2-30 after removal of the test panel from the subject's skin. In some embodiments, the evaluating is conducted on each of days 2, 4, 7, 14, and 21 after removal of the test panel from the subject's skin. In some embodiments, evaluating is conducted on one or more of day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, or day 30 after removal of the test panel from the subject's skin.

In some embodiments, correlating the quantitative severity of allergic contact dermatitis at the location of contact of each patch to the urushiol content of each patch corresponding comprises tabulating the reaction severity score for each patch and the urushiol concentration of each patch.

In some embodiments, calculating a dose-response for urushiol exposure can be performed by analyzing the tabulated the reaction severity score for each patch and the urushiol concentration of each patch in a statistical analysis program, e.g., SAS PROC GENMOD (SAS 9.4, SAS Institute, Cary, N.C.) to calculate a dose-response for urushiol exposure and resulting allergic contact dermatitis in a subject.

In another aspect, the present disclosure provides a method for determining if dermatitis of unknown etiology on the skin of a subject presenting with said dermatitis of unknown etiology at one or more locations on the skin of the subject is urushiol-induced allergic contact dermatitis, comprising applying a test panel as described herein to the skin of the subject for a predetermined period of time, removing the test panel from the skin of the subject, evaluating the urushiol-induced allergic contact dermatitis of the subject at the point of contact of each patch of the test panel, and comparing the urushiol-induced allergic contact dermatitis at the point of contact of each patch of the test panel with the dermatitis of unknown etiology at one more locations on the skin of the subject, wherein when the dermatitis at the point of contact of each patch of the test panel is substantially similar to the dermatitis at one more locations on the skin of the subject, the dermatitis of unknown etiology is determined to be urushiol-induced allergic contact dermatitis.

In some cases, subjects may exhibit dermatitis of unknown etiology that may appear similar to urushiol-induced allergic contact dermatitis. Since some forms of dermatitis are treatable, whereas there are few post-exposure treatment options for urushiol-induced allergic contact dermatitis, distinguishing between urushiol-induced allergic contact dermatitis and other, treatable types of dermatitis can rule out or confirm whether the dermatitis of unknown etiology is urushiol-induced allergic contact dermatitis. If the dermatitis of unknown etiology is not urushiol-induced allergic contact dermatitis, further diagnosis and/or treatment is indicated.

In some embodiments, the test panel is placed in contact with a subject's skin for predetermined period of time from about 1 hour to about 96 hours. In some embodiments, the predetermined period of time is from about 24 hours to about 72 hours. In some embodiments, the predetermined period of time is about 24, about 48, about 72, or about 96 hours. After removing the test panel from the subject's skin, the severity of the urushiol-induced contact dermatitis induced by each patch on the test panel is assessed. Such assessment can comprise visual inspection of the area in contact with each patch on the test panel and assigning a score to the reaction associated with each patch based on inspection. Severity of the urushiol-induced contact dermatitis induced by each patch on the test panel of reactions is independently graded according to standard morphology: 0 (no reaction), 1+ (non-vesicular with erythema, infiltration, and possibly papules), 2+ (edematous or vesicular reaction), 3+ (spreading, bullous, ulcerative reaction), +/− (macular erythema).

In some embodiments, the evaluating is conducted immediately after removal of the test panel from the subject's skin. In some embodiments, the evaluating is conducted one or more times. In some embodiments, the evaluating is conducted immediately after removal of the test panel from the subject's skin and on one or more of more of days 2-30 after removal of the test panel from the subject's skin.

In some embodiments, when the dermatitis at the point of contact of each patch of the test panel and the dermatitis of unknown etiology at one or more locations on the skin of the subject are substantially similar, the subject is diagnosed with is urushiol-induced allergic contact dermatitis. In some embodiments, when the dermatitis at the point of contact of each patch of the test panel and the dermatitis of unknown etiology at one or more locations on the skin of the subject are substantially different, the subject is diagnosed with dermatitis which is not urushiol-induced allergic contact dermatitis. In some embodiments, when the subject is diagnosed with dermatitis which is not urushiol-induced allergic contact dermatitis, further diagnosis may be conducted and/or treatment administered.

In another aspect, the present disclosure provides a method for determining if a treatment for urushiol-induced allergic contact dermatitis prevents or inhibits the severity of the urushiol-induced allergic contact dermatitis in a subject, comprising applying a first test panel as described herein to the skin of the subject for a predetermined period of time, removing the first test panel from the skin of the subject, evaluating the severity of allergic contact dermatitis of the subject at the point of contact of each patch of the first test panel at one or more times after removal of the test panel, administering the treatment to the subject, applying a second test panel as described herein to the skin of the subject for the same predetermined period of time after administering the treatment, removing the test panel from the skin of the subject, and evaluating the severity of allergic contact dermatitis of the subject at the point of contact of each patch of the second test panel at one or more times after administering the treatment, wherein when the severity of allergic contact dermatitis of the subject at the point of contact of each patch of the second test panel is less than the severity of allergic contact dermatitis of the subject at the point of contact of each patch of the first test panel, the treatment is determined to prevent or inhibit the severity of urushiol-induced allergic contact dermatitis in the subject.

In some embodiments, the first test panel is placed in contact with a subject's skin for predetermined period of time from about 1 hour to about 96 hours. In some embodiments, the predetermined period of time is from about 24 hours to about 72 hours. In some embodiments, the predetermined period of time is about 24, about 48, about 72, or about 96 hours. After removing the first test panel from the subject's skin, the severity of the urushiol-induced contact dermatitis induced by each patch on the test panel is assessed. Such assessment can comprise visual inspection of the area in contact with each patch on the test panel and assigning a score to the reaction associated with each patch based on inspection. Severity of the urushiol-induced contact dermatitis induced by each patch on the first and the second test panel of reactions is independently graded according to standard morphology: 0 (no reaction), 1+ (non-vesicular with erythema, infiltration, and possibly papules), 2+ (edematous or vesicular reaction), 3+ (spreading, bullous, ulcerative reaction), +/− (macular erythema).

In some embodiments, the evaluating is conducted immediately after removal of the first test panel from the subject's skin. In some embodiments, the evaluating is conducted one or more times. In some embodiments, the evaluating is conducted immediately after removal of the first test panel from the subject's skin and on one or more of more of days 2-30 after removal of the test panel from the subject's skin. In some embodiments, the evaluating is conducted on each of days 2, 4, 7, 14, and 21 after removal of the test panel from the subject's skin. In some embodiments, evaluating is conducted on one or more of day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, or day 30 after removal of the test panel from the subject's skin.

Application and evaluation of the first test panel of the first test panel enables the determination of the baseline response of the subject to the test panel prior to treatment with the treatment for urushiol-induced allergic contact dermatitis.

The present method then includes the step of administering a treatment for urushiol-induced allergic contact dermatitis to the subject after applying and evaluating the response to the first test panel. The treatment may be a small molecule, a peptide, an enzyme, an antibody, an oligonucleotide, a vaccine, or any therapy intended to prevent or inhibit the severity of the urushiol-induced allergic contact dermatitis in a subject.

In certain embodiments, the treatment for urushiol-induced allergic contact dermatitis is administered to the subject, thereby preventing urushiol-induced allergic contact dermatitis. In certain embodiments, the treatment for urushiol-induced allergic contact dermatitis is administered to the subject, thereby inhibiting urushiol-induced allergic contact dermatitis.

For use in in the present methods, the treatment for urushiol-induced allergic contact dermatitis can be administered to a subject by any mode that delivers the treatment for urushiol-induced allergic contact dermatitis to the desired location or surface. Administering a pharmaceutical composition comprising the treatment for urushiol-induced allergic contact dermatitis may be accomplished by any means known to the skilled artisan. Routes of administration include but are not limited to oral, intravenous, intramuscular, intraperitoneal, subcutaneous, direct injection (e.g., at the site of the urushiol-induced allergic contact dermatitis), mucosal, inhalation, and topical.

After administering to the subject, the treatment for urushiol-induced allergic contact dermatitis, a second test panel, substantially the same as the first test panel, is applied to the skin of the subject at a location different from that of the first test panel. In some embodiments, the second test panel is placed in contact with a subject's skin for the same predetermined period of time as the first test panel. After removing the second test panel from the subject's skin, the severity of the urushiol-induced contact dermatitis induced by each patch on the second. Such assessment is the same as that employed for the first test panel.

In some embodiments, wherein when the severity of allergic contact dermatitis of the subject at the point of contact of each patch of the second test panel is less than the severity of allergic contact dermatitis of the subject at the point of contact of each patch of the first test panel, the treatment is determined to prevent or inhibit the severity of urushiol-induced allergic contact dermatitis in the subject. In some embodiments, wherein when the severity of allergic contact dermatitis of the subject at the point of contact of each patch of the second test panel is the same as the severity of allergic contact dermatitis of the subject at the point of contact of each patch of the first test panel, the treatment is determined to be ineffective in treating or inhabiting urushiol-induced allergic contact dermatitis in the subject.

EXAMPLES

Having now described the present disclosure in detail, the same will be more clearly understood by reference to the following examples, which are included herewith for purposes of illustration only and are not intended to be limiting.

Example 1

Urushiol Patch Test using the T.R.U.E. TEST® System

The purpose of this study was to evaluate the safety and appropriate doses of urushiol required for a patch test based on the hydrogel delivery system utilized by T.R.U.E. Test (SmartPractice®, Phoenix, Ariz.). T.R.U.E. Test is approved by the United States Food and Drug Administration (FDA) as a biologic/device combination product with the intended use of patch testing for the diagnosis of contact allergy. Furthermore, the dose-response relationship between the doses of urushiol and the severity of response were examined.

Methods and Materials

After approval of the study protocol from the Penn State College of Medicine institutional review board, nine volunteer subjects with a documented history of allergic contact dermatitis to poison ivy, oak or sumac were entered into the study after informed consent was obtained. None of the subjects was immunocompromised. Subjects did not undergo treatment with systemic or topical corticosteroids for at least 1 month prior to study entry or antihistamines for at least two weeks prior to the study entry through the end of the study period.

Urushiols were supplied by ElSohly Laboratories, Inc. (Oxford, Miss.). Urushiols are purified following the general procedure previously described by ElSohly et al.[6] Briefly, organic solvent extraction (ethanol) of poison ivy leaves and small stems was followed by partitioning of the extract between water and chloroform and silica gel chromatography of the chloroform fraction using chloroform as the elution solvent. Select fractions of the column eluate are dried and further extracted by partition in organic solvents (acetonitrile and hexane) with the acetonitrile portion collected and dried. The final extract contains 61.5% w/w urushiols, predominately comprising the tri-unsaturated congener of pentadecylcatechol (PDC), together with some mono- and di-unsaturated congeners of PDC as well as a small amount of PDC. For the preparation of the skin testing patches the urushiols extract is dissolved in ethanol to create a solution of 5 mg/mL urushiols (based on 61.5% urushiols content). The ethanolic urushiols solution is stored in amber glass vials at 2-8° C. and was evaluated for stability through twelve months. The refrigerated and frozen samples of urushiols solution, analyzed by GC-FID for urushiol concentration on days 0, 7, 14, 29, 57, 97, 185, 275 and 365, were shown to be stable without undergoing degradation for at least 12 months.

The urushiol patches were prepared by mixing an appropriate amount of the ethanolic urushiol solution with PVP and coating a sheet of occlusive polyester with the mixture of ethanolic urushiol solution and PVP. The desired amount of urushiol ethanolic solution was mixed with the PVP excipient until a gel with a uniform concentration of urushiol was achieved. The gel was then allowed to swell appropriately and centrifuged as necessary to remove air bubbles. The occlusive polyester sheet was pre-treated to apply an electrostatic charge and then the urushiol gel mixture was applied to the polyester sheet. The urushiol gel coated sheets were dried, trimmed and packed into a labeled laminate foil pouch and stored at 2-8° C. Stability of the urushiol in the urushiol-gel coated sheets was observed for at least twelve months when stored at 2-8° C.

To prepare the panel test, urushiol patches at 4 strengths of 0.041 µg, 0.081 µg, 0.16 µg, 0.32 µg plus one patch with a negative control were cut into small square patches (approximately 0.81 cm$^2$) and placed randomly onto an adhesive support of surgical tape. The finished test panels were covered with a protective sheet and sealed in a laminated foil pouch. They were then labeled and dispensed for use on the study subjects.[7,8,9]

The panel comprising randomly positioned patches of urushiol at four strengths and a negative control was applied on skin on the back of each subject. Once administered (on day 0), the patch test remained on the subject for two days and was then removed. Upon removal on day 2, the first assessment and interpretation of the results was performed. Additional assessments and interpretations were performed on days 4, 7, 14, and 21. Study subjects and the investigator were blind to the arrangement of the test patches and placebo on each test panel. Severity of the reactions were graded according to standard morphology: 0 (no reaction), 1+ (non-vesicular with erythema, infiltration, and possibly papules), 2+ (edematous or vesicular reaction), 3+ (spreading, bullous, ulcerative reaction), +/− (macular erythema). Symptoms such as pruritus and burning, and any adverse events were assessed and documented. Irritancy was differentiated from a true allergic contact dermatitis response by the duration of the reaction. Response to treatment, which was initially coded as 0, +/−, 1, 2, 3, was recoded in a binary fashion as follows: 0=no response, all other values=response. A repeated measures binary logistic regression model was fit with SAS PROC GENMOD (SAS 9.4, SAS Institute, Cary, N.C.) using an autoregressive correlation structure. Both dosage and time were included as categorical explanatory variables. However, the model did not include an interaction term because of the limited number of subjects. Odds ratio estimates for each non-zero dosage versus control were obtained by exponentiating the appropriate parameter estimates.

Results

Nine subjects were enrolled in the study and they included 3 male and 6 female individuals aged 22 to 59 (mean age, 46 years) All subjects completed the study. One subject had a mild flare of dyshidrotic hand eczema, which was treated with clobetasol cream for one day.

Each of the doses of urushiol compared to placebo on the test panel yielded a reaction. Despite the limitation of a small sample size, the odds ratio for each of the doses were much greater than and did not include 1 (the null value), which confirms that each dose of urushiol used for each patch on the test panel yielded a reaction (Table 1). Furthermore, the odds ratio was greater as the dose of urushiol increased, which indicates that higher doses yield more severe reactions compared to placebo in all of the days.

TABLE 1

Odds ratio of the reactions elicited by the various doses of urushiol compared to placebo

| Dose | Odds ratio | 95% Confidence Interval |
| --- | --- | --- |
| 0.041 | 475.5 | (30.7, 7376.8) |
| 0.081 | 1927 | (132.7, 27981.5) |
| 0.16 | 3204.1 | (185.7, 55270.8) |
| 0.32 | 7188.9 | (378.0, 136721.3) |

Figure 2:
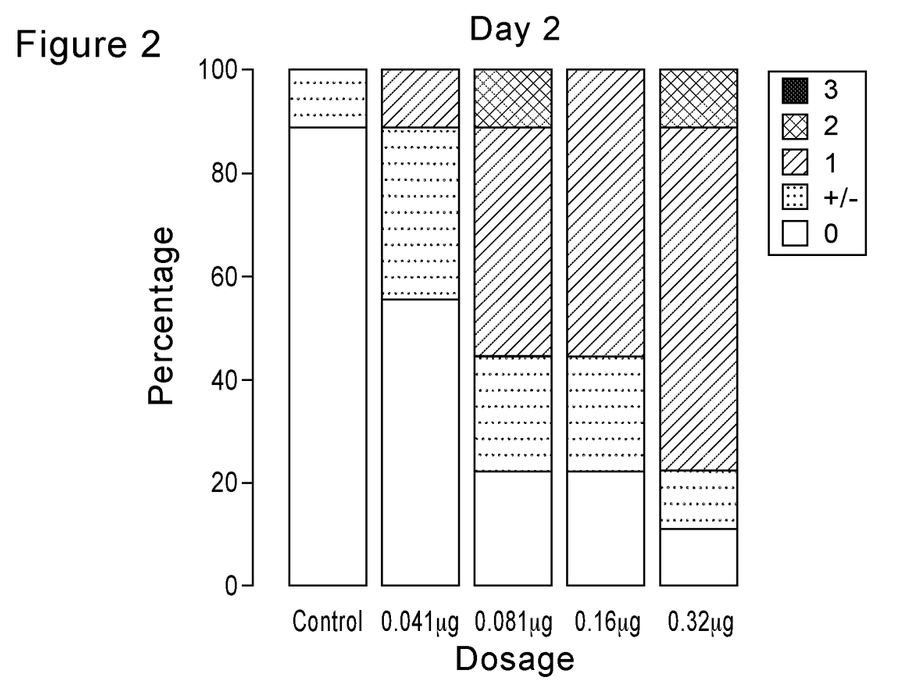
FIG. 2 is a bar graph showing scoring of urushiol-induced allergic contact dermatitis response for various doses of urushiol from a test panel comprising a control panel, a patch comprising 0.041 μg of urushiol, a patch comprising 0.081 μg of urushiol, a patch comprising 0.16 μg of urushiol, and a patch comprising 0.32 μg of urushiol at day 2 after application of the test panel.
Figure 3:
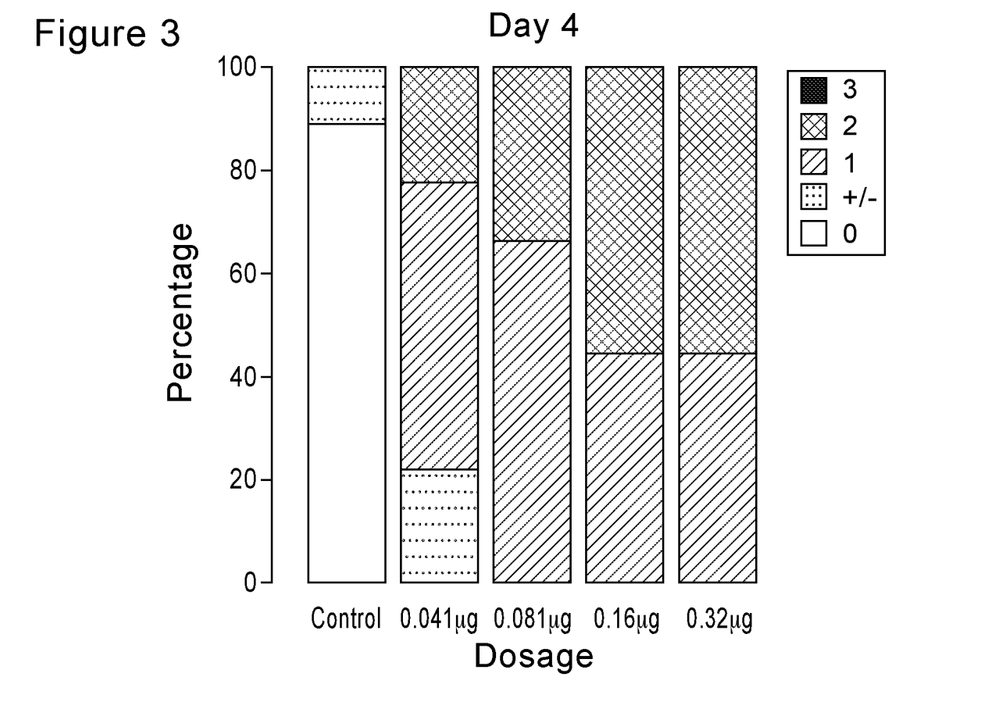
FIG. 3 is a bar graph showing scoring of urushiol-induced allergic contact dermatitis response for various doses of urushiol from a test panel comprising a control panel, a patch comprising 0.041 μg of urushiol, a patch comprising 0.081 μg of urushiol, a patch comprising 0.16 μg of urushiol, and a patch comprising 0.32 μg of urushiol at day 4 after application of the test panel.
Figure 4:
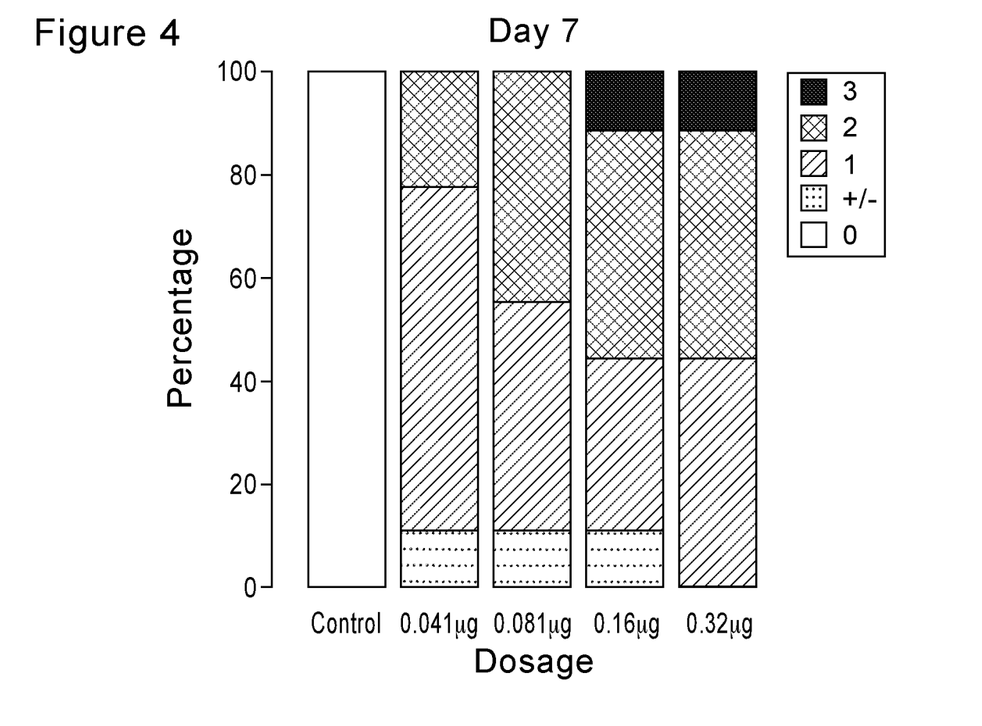
FIG. 4 is a bar graph showing scoring of urushiol-induced allergic contact dermatitis response for various doses of urushiol from a test panel comprising a control panel, a patch comprising 0.041 μg of urushiol, a patch comprising 0.081 μg of urushiol, a patch comprising 0.16 μg of urushiol, and a patch comprising 0.32 μg of urushiol at day 7 after application of the test panel.
Figure 5:
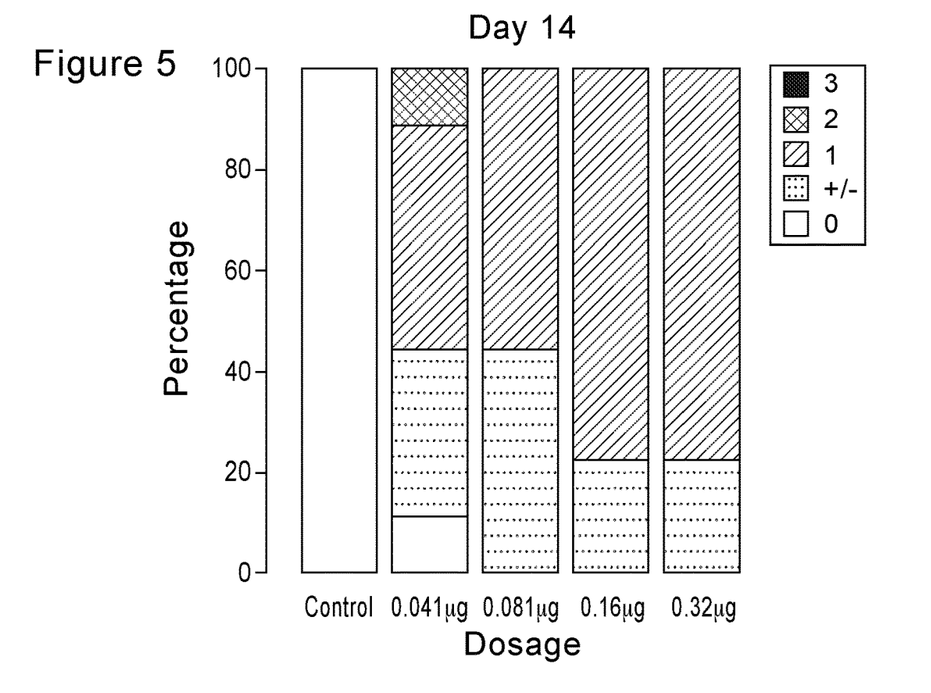
FIG. 5 is a bar graph showing scoring of urushiol-induced allergic contact dermatitis response for various doses of urushiol from a test panel comprising a control panel, a patch comprising 0.041 μg of urushiol, a patch comprising 0.081 μg of urushiol, a patch comprising 0.16 μg of urushiol, and a patch comprising 0.32 μg of urushiol at day 14 after application of the test panel.
Figure 6:
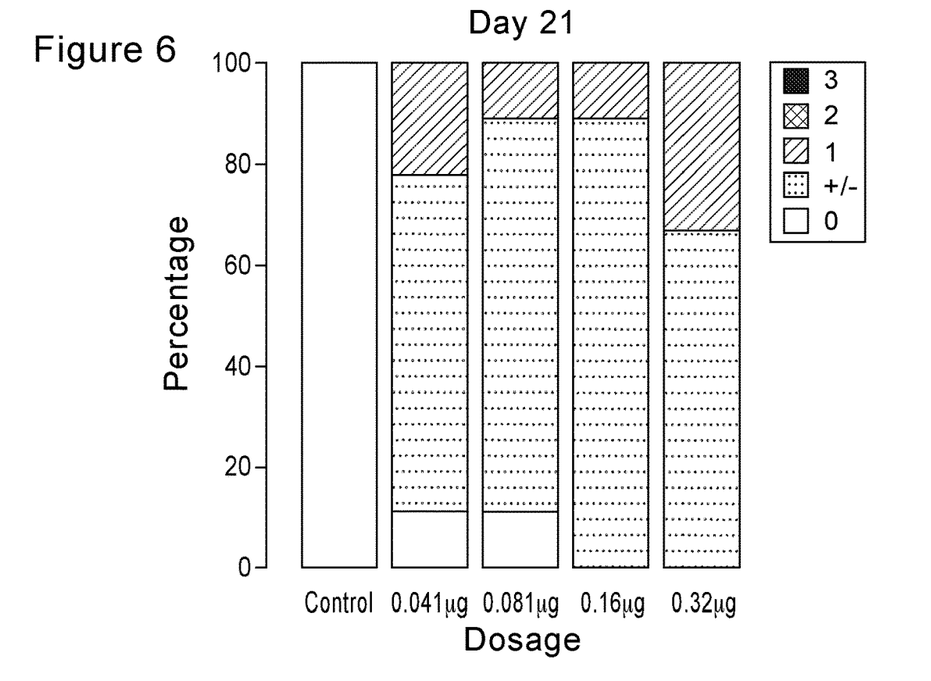
FIG. 6 is a bar graph showing scoring of urushiol-induced allergic contact dermatitis response for various doses of urushiol from a test panel comprising comprising a control panel, a patch comprising 0.041 μg of urushiol, a patch comprising 0.081 μg of urushiol, a patch comprising 0.16 μg of urushiol, and a patch comprising 0.32 μg of urushiol at day 21 after application of the test panel.

On day 2, reactions varied from +/− to 2+ (FIG. 2). On day 4 (FIG. 3), reactions were stronger than day 2 (FIG. 2). On day 7 (FIG. 4), only one subject had a 3+ reaction. On day 14 (FIG. 5), reactions were less intense than days 4 (FIG. 3) and 7 (FIG. 4) and on day 21 (FIG. 6), all subjects had the weakest reactions.

Figure 7:
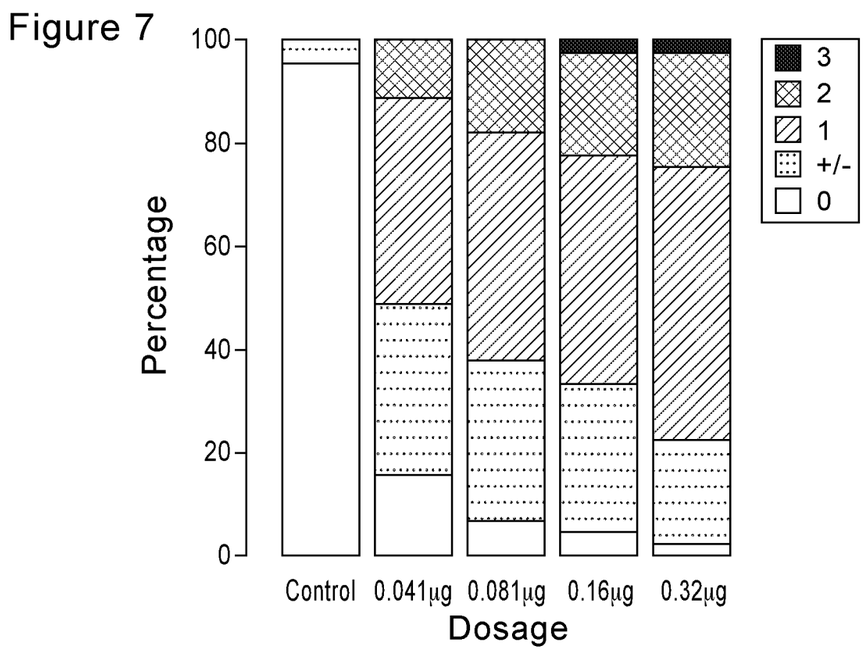
FIG. 7 is a bar graph showing composite scoring of the intensity of urushiol-induced allergic contact dermatitis response for various doses of urushiol from a test panel comprising a control panel, a patch comprising 0.041 μg of urushiol, a patch comprising 0.081 μg of urushiol, a patch comprising 0.16 μg of urushiol, and a patch comprising 0.32 μg of urushiol for all subjects at all assessment times after application of the test panel.
Figure 8:
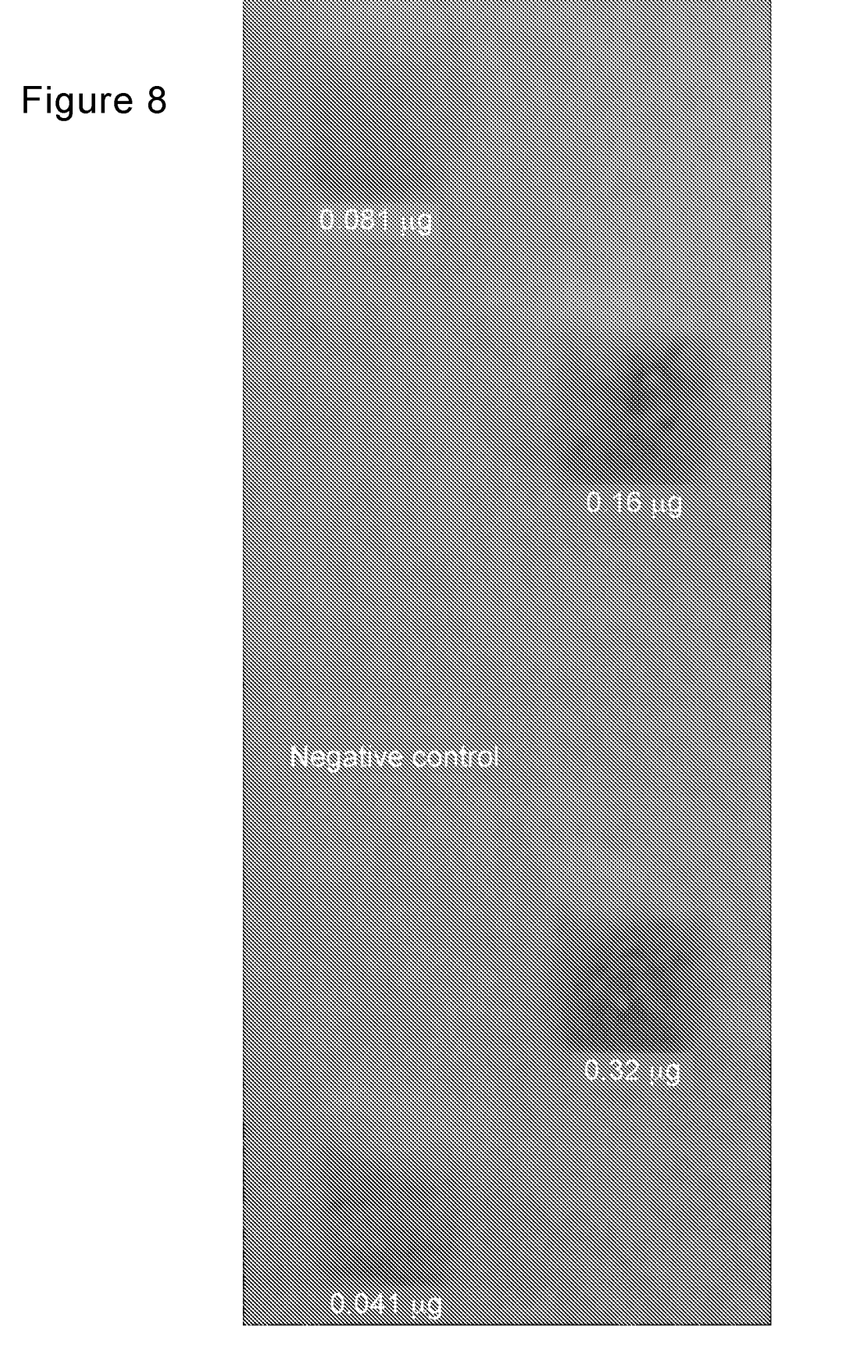
FIG. 8 is a picture showing a subject's skin at the point of contact of each patch of a test panel comprising a control panel, a patch comprising 0.041 μg of urushiol, a patch comprising 0.081 μg of urushiol, a patch comprising 0.16 μg of urushiol, and a patch comprising 0.32 μg of urushiol at day 7 after application of the test panel, The reactions for the control panel, the patch comprising 0.041 μg of urushiol, the patch comprising 0.081 μg of urushiol, the patch comprising 0.16 μg of urushiol, and the patch comprising 0.32 μg of urushiol, 0, 2+, 2+, 3+, and 3+, respectively.
Figure 9:
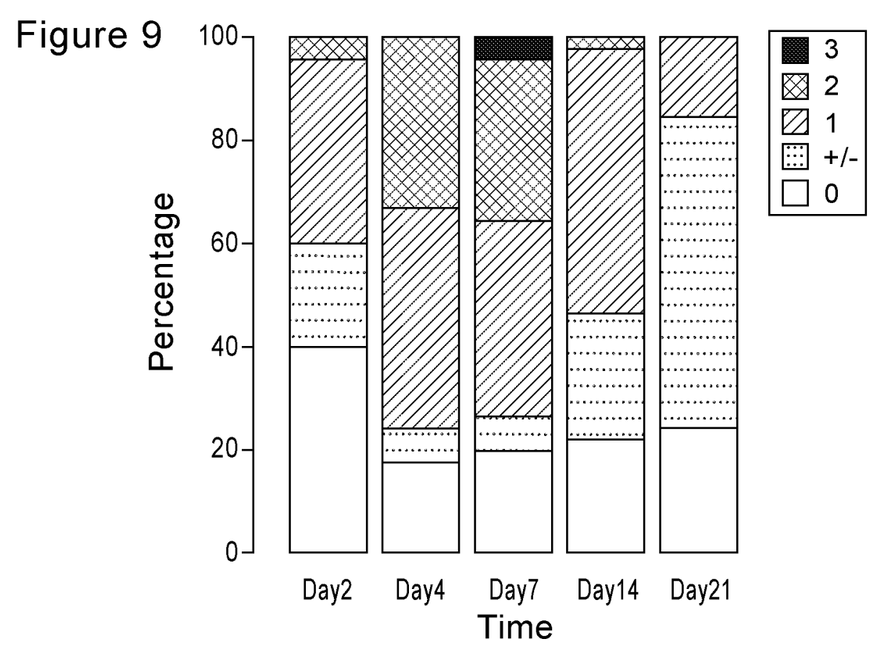
FIG. 9 is a bar graph showing composite scoring of the intensity of urushiol-induced allergic contact dermatitis response for all urushiol concentrations for all subjects from a test panel comprising a control panel, a patch comprising 0.041 μg of urushiol, a patch comprising 0.081 μg of urushiol, a patch comprising 0.16 μg of urushiol, and a patch comprising 0.32 μg of urushiol for all subjects at day 2, day 4, day 7, day 14, and day 21 after application of the test panel, showing that peak of severity of response was on days 4 or 7.

FIG. 7 illustrates the intensity of the reaction for the various doses. There appears to be a dose-response relationship between the dose of urushiol and the reaction that it yields. For instance, the strongest dose, 0.32 µg, appears to yield the strongest reaction, reflected by the highest number of subjects with 1+, 2+, or 3+ reaction compared to the weaker doses. Furthermore, the only time there was a 3+ reaction was in the two higher doses, 0.16 µg and 0.32 µg. One subject on day 4 had a 3+ reaction to the two higher doses and a 2+ reaction to the two lower doses (FIG. 8). Moreover, FIG. 9 demonstrates that the peak of severity of response was on days 4 or 7 for all subjects.

Discussion

The pathophysiology of allergic contact dermatitis is a T-lymphocyte-mediated delayed type hypersensitivity reaction. Upon initial contact with poison ivy, poison oak, poison sumac, urushiol catechols avidly bind to and penetrate the skin, where they become oxidized to quinone intermediates and bind to surface proteins of Langerhans cells and macrophages. These antigen-presenting cells internalize and process the antigen, migrate to regional lymph nodes, and present processed antigen to CD4 T-helper lymphocytes, which results in an activated T cell that forms a clone of urushiol-specific T-effector and T-memory lymphocyte.[10] Subsequent contact with poison ivy, poison oak, and poison sumac elicits a cell-mediated cytotoxic immune response by the clonal lymphocytes, which results in destruction of epidermal cells and activation of dermal vasculature.

Typically, a sensitized individual develops an intensely pruritic, erythematous eruption within 24 to 48 hours but can range from 5 hours to 15 days.[11] This reaction is described as streaks or areas of erythema and edematous papules, which precede vesicles and bullae. The mildest reaction (+/− or 1+) generally lack vesicles. On the other hand, severe reactions (2+ or 3+) can be characterized by vesicles to confluent bullae. Individual variations in the course of experimentally-induced allergic contact dermatitis from urushiol in previously sensitized adults do exist. One study documented the range of individual variations in both reaction time and severity, which most likely represent differences in underlying immune responses between individuals.[11] For instance, the onset of reactions ranged from 4 hours to 4 days, peak reactions occurred from 1 to 14 days, and maximum severity of reactions ranged from 2+ to 3+ (erythema, edema, vesiculation, ulcerative breakdown). This study likewise confirms that individuals vary in both severity of response and reaction time. Most of our subjects had a mild to moderate reaction (+/−, 1+, 2+). Only one subject had a 3+ reaction, characterized by a spreading, bullous, ulcerative reaction. The peak intensity of reaction, regardless of the dose of urushiol, was seen in days 4 or 7 for all subjects. This also verifies that the reaction elicited is a true allergic contact dermatitis reaction rather than an irritant contact dermatitis reaction because typically at 96 hours, irritant responses may be faded while allergic ones may continue unabated.[12] Furthermore, a dose-response relationship for the 4 doses of urushiol in the test panel was observed. Stronger doses of urushiol appears to elicit a stronger reaction. Similarly, Epstein et al. found a dose-response relationship of dilutions of urushiol in the number of subjects with a positive reaction.[13]

REFERENCES CITED

1. Pariser D M, Ceilley R I, Lefkovits A M, Katz B E, Palter A S. Poison ivy, oak and sumac. *Derm. Insights.* 2003; 4:26-28.
2. Marks J G, Anderson B E, DeLeo V A. Contact and occupational dermatology. Jaypee Brothers Medical Publishers (P) Ltd, New Delhi, India. 2016.
3. Marks J G. Poison ivy and Poison oak allergic contact dermatitis. J Allergy Clin Immunol 1989; 9:497-506.
4. Fisher A A. Poison ivy/oak/sumac. Part II: Specific features. Cutis 1996; 56:22.
5. McGovern T W, Barkley T M. Botanical dermatology. Int J Dermatol 1998; 37:321.
6. ElSohly M A, Adawadkar P D, MA CU and Turner C T. Separation and Characterization of Poison ivy and poison oak components. J. Natural Products, 1982; (5): 532-538.
7. ElSohly M A, Gul W, Ashfaq M, Manly S P. Compositions for prevention/prophylactic treatment of poison ivy dermatitis. U.S. Pat. No. 8,486,998 B2, 2013.
8. ElSohly M A, Gul W, Ashfaq M, Manly S P. Compositions for prevention/prophylactic treatment of poison ivy dermatitis. U.S. Pat. No. 9,029,417 B2, 2015.
9. ElSohly M A, Gul W, Ashfaq M, Manly S P. Compositions for prevention/prophylactic treatment of poison ivy dermatitis. U.S. Pat. No. 9,408,822 B2, 2016.
10. Gladman A C. *Toxicodendron* Dermatitis: Poison ivy, oak, and sumac. Wilderness and Environmental Medicine. 2006; 17:120-128.
11. Williams J V, Light J, Marks J G. Individual variations in allergic contact dermatitis from urushiol. Arch Dermatol. 1999; 135:1002-1003.
12. Dahl M V, Pass F, Trancik R J. *Toxicodendron* Antigen Patch Test. Arch Dermatol 1984; 120:1022-1024.
13. Epstein W L, Baer H, Dawson C R, Khurana R G. Poison oak hyposensitization. Arch. Dermatol. 1974; 109:356-60.
14. Fisher A A. Poison ivy/oak dermatitis. Part 1: prevention—soap and water, topical barriers, hyposensitization. Cutis. 1996; 57:384-386.
15. Stibich A S, Yagan M, Sharma V, Herndon B, Montgomery C. Cost-effective post-exposure prevention of poison ivy dermatitis. Int J Dermatol. 2000; 39:515-518.
16. Davila A, Lucas J, Laurora M, Jacoby J, Reed J, Heller M. A new topical agent, Zanfel, ameliorates urushiol-induced *Toxicodendron* allergic contact dermatitis [abstract 364]. Annals Emerg Med. 2003; 42(suppl 4):s98.
17. Smith W B, Baunchalk J M, Grabski W J. Lack of efficacy of a barrier cream in preventing Rhus Dermatitis. Arch Dermatol. 1993; 129:787-788.
18. Marks J G, Fowler J F, Sherertz E F, Rietschel R L. Prevention of poison ivy and poison oak allergic contact dermatitis by quaternium-18 bentonite. J Am Acad Dermatol. 1995; 33:212-6.
19. Marks J G, Trautlein J J, Epstein W L, Laws D M, Sicard G R. Oral hyposensitization to poison ivy and poison oak. Arch Dermatol. 1987; 23:476-478.
20. Epstein W L. Rhus Dermatitis. Ped Clinics of North Am. 1959; 843-52.

What is claimed is:
1. A urushiol-containing epicutaneous patch comprising:
   a. a support material; and
   b. a urushiol-containing film on a surface of the support material;
   wherein the surface of the support material is coated with the urushiol-containing film,
   wherein the urushiol-containing film comprises from about 0.04 µg to about 0.5 µg of urushiol, and
   the urushiol comprises one or more of pentadecylcatechol, 3-n-heptadecylcatechol, mono-, di-, or tri-unsaturated congeners of pentadecylcatechol, 3-n-heptadecylcatechol with one, two, three or more olefins or combinations thereof.
2. The patch of claim 1, wherein the urushiol-containing film comprises polyvinylpyrrolidone.
3. The patch of claim 1, wherein the urushiol-containing film comprises from about 0.1 µg to about 0.2 µg of urushiol.
4. The patch of claim 1, wherein the urushiol-containing film comprises from about 0.2 µg to about 0.4 µg of urushiol.
5. The patch of claim 1, wherein the patch has a size of from about 0.2 cm$^2$ to about 1 cm$^2$.
6. The patch of claim 1, wherein the patch has a size of about 0.81 cm$^2$.
7. A test panel for assessment of allergic contact dermatitis in a subject resulting from exposure to urushiol, comprising at least 1 patch of claim 1.
8. A test panel for assessment of allergic contact dermatitis in a subject resulting from exposure to urushiol, comprising at least 2 patches of claim 1; wherein each patch comprises a different amount of urushiol.
9. A test panel for assessment of allergic contact dermatitis in a subject resulting from exposure to urushiol, comprising 1 to 4 patches of claim 1; wherein each patch comprises a different amount of urushiol.
10. The test panel of claim 9, further comprising a control patch substantially identical to said patches but which does not contain urushiol.
11. The test panel of claim 9, comprising:
   a first patch comprising about 0.041 µg of urushiol; a second patch comprising about 0.081 µg of urushiol;
   a third patch comprising about 0.16 µg of urushiol;
   a fourth patch comprising about 0.32 µg of urushiol; and
   a control patch substantially identical to said first, second, third, and fourth patches, but which does not contain urushiol.
12. A method for assessing sensitivity to urushiol-induced allergic contact dermatitis in a subject, comprising:
   applying a test panel of claim 7 to the skin of the subject for a predetermined period of time;
   removing the test panel from the skin of the subject; and
   evaluating the severity of allergic contact dermatitis of the subject at the point of contact of each patch of the test panel at one or more times after removal of the test panel.
13. The method of claim 12, wherein the predetermined period of time is from about 1 hour to about 96 hours.
14. The method of claim 12, wherein said evaluating is conducted:
   (i) immediately after removal of the test panel from the subject's skin; or

(ii) on one or more of days 2-30 after removal of the test panel from the subject's skin.

15. A method for calculating a dose-response for urushiol exposure and resulting severity of allergic contact dermatitis in a subject, comprising:
applying a test panel of claim 7 for a predetermined period of time; removing the test panel from the skin of the subject;
quantifying the severity of allergic contact dermatitis of the subject at the point of contact of each patch of said test panel;
correlating the quantitative severity of allergic contact dermatitis at the location of contact of each patch of said test panel to the urushiol content of each patch corresponding to said location of contact of each patch; and
calculating a dose-response for urushiol exposure and resulting allergic contact dermatitis in a subject from said quantified severity of allergic contact dermatitis to the urushiol content of each patch at the location corresponding to said quantified severity.

16. A method for determining if dermatitis of unknown etiology on the skin of a subject presenting with said dermatitis of unknown etiology at one or more locations on the skin of the subject is urushiol-induced allergic contact dermatitis, comprising:
applying a test panel of claim 7 to the skin of the subject for a predetermined period of time;
evaluating the urushiol-induced allergic contact dermatitis of the subject at the point of contact of each patch of the test panel; and
comparing the urushiol-induced allergic contact dermatitis at the point of contact of each patch of the test panel with the dermatitis of unknown etiology at one more locations on the skin of the subject;
wherein when the dermatitis at the point of contact of each patch of the test panel is substantially similar to the dermatitis of unknown etiology at one more locations on the skin of the subject, the dermatitis of unknown etiology is urushiol-induced allergic contact dermatitis.

17. A method for determining if a treatment for urushiol-induced allergic contact dermatitis prevents or inhibits the severity of the urushiol-induced allergic contact dermatitis in a subject, comprising:
applying a first test panel of claim 7 to the skin of the subject for a predetermined period of time;
removing the first test panel from the skin of the subject;
evaluating the severity of allergic contact dermatitis of the subject at the point of contact of each patch of the first test panel at one or more times after removal of the test panel;
administering the treatment to the subject;
applying a second test panel of claim 7 to the skin of the subject for the same predetermined period of time after administering the treatment;
removing the second test panel from the skin of the subject; and
evaluating the severity of allergic contact dermatitis of the subject at the point of contact of each patch of the second test panel at one or more times after administering the treatment;
wherein when the severity of allergic contact dermatitis of the subject at the point of contact of each patch of the second test panel is less than the severity of allergic contact dermatitis of the subject at the point of contact of each patch of the first test panel, the treatment is determined to prevent or inhibit the severity of urushiol-induced allergic contact dermatitis in the subject.

18. The patch of claim 1, wherein the urushiol-containing film comprises from about 0.075 µg to about 0.085 µg of urushiol.

19. A urushiol-containing epicutaneous patch comprising:
a. a support material; and
b. a urushiol-containing film on a surface of the support material;
wherein the surface of the support material is coated with the urushiol-containing film,
wherein the urushiol-containing film comprises about 0.001, about 0.005, about 0.010, about 0.015, about 0.020, about 0.025, about 0.030, about 0.035, about 0.040, about 0.045, about 0.050, about 0.060, about 0.070, about 0.080, about 0.090, about 0.1, about 0.15, about 0.2, about 0.25, about 0.3, about 0.35, about 0.4, about 0.45, or about 0.5 µg of urushiol, and
the urushiol comprises one or more of pentadecylcatechol, 3-n-heptadecylcatechol, mono-, di-, or tri-unsaturated congeners of pentadecylcatechol, 3-n-heptadecylcatechol with one, two, three or more olefins or combinations thereof.

* * * * *